United States Patent [19]
Fischer, deceased

[11] 3,975,179
[45] Aug. 17, 1976

[54] HERBICIDE MIXTURES OF 3-LOWER ALKYL-2,1,3-BENZOTHIADIAZINONE-(4)-2,2-DIOXIDES AND THIAZOLES

[75] Inventor: Adolf Fischer, deceased, late of Mutterstadt, Germany, by Caecilia Emma Fischer, legal representative

[73] Assignee: BASF Aktiengesellschaft, Ludwigshafen (Rhine), Germany

[22] Filed: Feb. 10, 1975

[21] Appl. No.: 548,390

Related U.S. Application Data

[62] Division of Ser. No. 432,675, Jan. 11, 1974, Pat. No. 3,909,232, which is a division of Ser. No. 343,629, March 22, 1973, Pat. No. 3,888,655.

[30] Foreign Application Priority Data

Apr. 13, 1972 Germany.......................... 2217722

[52] U.S. Cl............................................ 71/90; 71/91
[51] Int. Cl.² ...................... A01N 9/12; A01N 9/16
[58] Field of Search................................ 71/91, 90

[56] References Cited
UNITED STATES PATENTS
3,515,538  6/1970  Ueno et al............................ 71/90
3,708,277  1/1973  Zeidler et al. ........................ 71/91

OTHER PUBLICATIONS

Fischer I, "Herbicidal Compositions" (1971) CA 74 No. 110,714w, (1971).
Fischer II, "Herbicidal Compositions, etc.," (1971) CA 75 No. 75217h, (1971).

Primary Examiner—Glennon H. Hollrah
Attorney, Agent, or Firm—Johnston, Keil, Thompson & Shurtleff

[57] ABSTRACT

Herbicide compositions of mixtures in the weight ratio of 5:1 to 1:5 of (a) 3-lower alkyl-2,1,3-benzothiadiazinone-(4)-2,2-dioxide or a salt thereof and (b) a compound of the formula

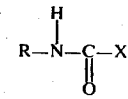

where R denotes a 5-chloro-4-methylthiazol-2-yl radical and X denotes lower alkyl.

8 Claims, No Drawings

HERBICIDE MIXTURES OF 3-LOWER ALKYL-2,1,3-BENZOTHIADIAZINONE-(4)-2,2-DIOXIDES AND THIAZOLES

RELATED APPICATION

This application is a division of my copending application Ser. No. 432,675, filed Jan. 11, 1974, now U.S. Pat. No. 3,909,232, which in turn is a division of my application Ser. No. 343,629, filed Mar. 22, 1973, now U.S. Pat. No. 3,888,655, the disclosures of which are incorporated herein by reference.

The present invention relates to a herbicide comprising a composition of several active ingredients.

It is known that substituted phenyl ether, carbamates, terephthalates, acid amides, benzoic acids, fluorencecarboxylic acids and benzothiadiazinones have a herbicidal action. However, this action is poor.

I have now found that a composition of
a. a compound of the formula

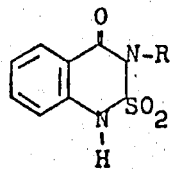

where R denotes lower alkyl of a maximum of 4 carbon atoms, or its salts, such as alkali metal, alkaline earth metal, ammonium, hydroxyalkylammonium, alkylammonium and hydrazine salts, e.g. salts with sodium, lithium, potassium, calcium, iron, methylammonium, trimethylammonium, ethylammonium, diethanolammonium, ethanolammonium, dimethylamine, dimethylethanolamine, hydrazine and phenylhydrazine, and
b. a compound of the formula

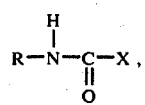

where R denotes a 5-chloro-4-methylthiazol-2-yl radical and X denotes lower alkyl have a herbicidal action superior to that of their individual components.

Active ingredients $a$ and $b$ may be applied in amounts of 0.5 to 5 kg per hectare.

The weight ratio of $a:b$ is from 5:1 to 1:5, preferably from 3:1 to 1:3.

The compositions of the invention are suitable for controlling unwanted plants, e.g. dicotyledonous seed weeds, monocotyledonous grassy seed weeds and Cyperaceae in crops such as cereals, rice, soybeans, Indian corn, potatoes, peas, and beans.

The compositions may be applied to the loci of the plants, pre- and/or postemergence.

The agents according to the invention may be used as solutions emulsions, suspensions oil dispersions, granules or dusts. The form of application depends entirely on the purpose for which the agents are being used; in any case it should ensure a fine distribution of the active ingredient.

For the preparation of solutions to be sprayed direct, mineral oil fractions of medium to high boiling point, such as kerosene or diesel oil, further coal-tar oils and oils of vegetable or mineral origin, and cyclic hydrocarbons such as tetrahydronaphthalene and alkylated naphthalenes are suitable.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g., polyethylene oxide adducts. Concentrates which are suitable for dilution with water may be prepared from active ingredient, wetting agent, adherent, emulsifying or dispersing agent and possibly solvent. Oils of various types may be added to ready-to-use spray liquors.

Dusts may be prepared by mixing or grinding the active ingredients with a solid carrier, e.g., clay or fertilizers.

Granules may be prepared by bonding the active ingredients to solid carriers.

Directly sprayable dispersions may also be prepared with oils.

The new compounds may be mixed with fertilizers, insecticides, fungicides and other herbicides.

EXAMPLE 1

The plants wheat (*Triticum aestivum*), barley (*Hordeum vulgare*), wild oats (*Avena fatua*), slender foxtail (*Alopecurus myosuroides*), catchweed bedstraw (*Galium aparine*), chickweed (*Stellaria media*) and henbit (*Lamium amplexicaule*) were treated at a growth height of 4 to 20 cm with the following amounts of the following individual active ingredients and compositions thereof, each active ingredient and each composition being emulsified or dispersed in 500 liters of water per hectare:

I  4-chlorobutyn-2-yl-1 N-3-chlorophenylcarbamate, 1 and 2 kg per hectare;
II  5-chloro-4-methyl-2-propionamide thiazole, 2 and 3 kg per hectare;
III  3,5-dibromo-4-hydroxybenzaldoxime-O-(2',4'-dinitrophenyl)-ether, 0.75 and 1.5 kg per hectare;
IV  9-hydroxyfluorenecarboxylic acid-(9), 1 and 3 kg per hectare;
V  3-isopropyl-2,1,3-benzothiadiazinone-(4)-2,2-dioxide, 0.75, 1.5, 2 and 3 kg per hectare;
I + V 1.0 + 1.0 kg per hectare;
II + V 2.0 + 1.0 kg per hectare;
III + V 0.75 + 0.75 kg per hectare;
IV + V 1.0 + 2.0 kg per hectare.

After 8 to 12 days it was ascertained that the compositions had a better overall action than the individual active ingredients, combined with good crop plant compatibility. The results are given below:

| Active ingredient kg/ha | I | | II | | III | | IV | | V | | | | I+V | II+V | III+V | IV+V |
|---|---|---|---|---|---|---|---|---|---|---|---|---|---|---|---|---|
| | 1 | 2 | 2 | 3 | 0.75 | 1.5 | 1 | 3 | 0.75 | 1 | 1.5 | 2 | 3 | 1+1 | 2+1 | 0.75+0.75 | 1+2 |
| *Triticum aestivum* | 0 | 0 | 10 | 20 | 0 | 10 | 0 | 0 | 0 | 0 | 0 | 0 | 0 | 0 | 10 | 0 | 0 |
| *Hordeum vulgare* | 0 | 0 | 10 | 20 | 5 | 15 | 0 | 15 | 0 | 0 | 0 | 0 | 0 | 0 | 10 | 0 | 0 |

-continued

| Active ingredient kg/ha | I 1 | I 2 | II 2 | II 3 | III 0.75 | III 1.5 | IV 1 | IV 3 | V 0.75 | V 1 | V 1.5 | V 2 | V 3 | I+V 1+1 | II+V 2+1 | III+V 0.75+0.75 | IV+V 1+2 |
|---|---|---|---|---|---|---|---|---|---|---|---|---|---|---|---|---|---|
| Avena fatua | 70 | 90 | 50 | 70 | — | — | — | — | 5 | 5 | 5 | 5 | 10 | 85 | 80 | — | — |
| Alopecurus myosuroides | 60 | 85 | 50 | 75 | — | — | — | — | 5 | 5 | 10 | 10 | 15 | 80 | 80 | — | — |
| Galium aparine | 5 | 10 | 30 | 45 | 20 | 45 | 30 | 85 | 35 | 40 | 60 | 70 | 80 | 80 | 90 | 90 | 100 |
| Stellaria media | 10 | 30 | 40 | 65 | 30 | 70 | 30 | 90 | 40 | 60 | 70 | 90 | 90 | 90 | 100 | 100 | 100 |
| Lamium amplexicaule | 5 | 10 | 5 | 10 | 45 | 80 | 30 | 95 | 30 | 40 | 50 | 60 | 70 | 75 | 75 | 100 | 100 |

0 = no damage
100 = complete destruction

EXAMPLE 2

In the greenhouse, various plants were treated at a growth height of from 3 to 23 cm with the following amounts of the following individual active ingredients and compositions thereof as emulsions, dispersion, aqueous solutions or suspensions:

I  3-isopropyl-2,1,3-benzothiadiazinone-(4)-2,2-dioxide, 0.5, 0.75, 1 and 1.5 kg/ha;
II  3-isopropyl-2,1,3-benzothiadiazinone-(4)-2,2-dioxide, sodium salt, 0.5, 0.75, 1 and 1.5 kg/ha;
III 5-chloro-4-methyl-2-propionamide thiazole, 0.5, 0.75, 1 and 1.5 kg/ha;
IV 3-isopropyl-2,1,3-benzothiadiazinone-(4)-2,2-dioxide, dimethylamine salt, 0.5, 0.75, 1 and 1.5 kg/ha;
V 3-isopropyl-2,1,3-benzothiadiazinone-(4)-2,2-dioxide, diethanolamine salt, 0.5, 0.75, 1 and 1.5 kg/ha;
I+III, II+III, IV+III and V+III, each at rates of 0.5+1, 1+0.5 and 0.75+0.75 kg/ha.

After 2 and 3 weeks it was ascertained that the compositions had a better herbicidal action than their components, combined with the same crop plant compatibility.

The results are given below:

EXAMPLE 3

In the greenhouse, various plants were treated at a height of from 3 to 22 cm with the following individual active ingredients and compositions thereof as emulsions, dispersions, suspensions or aqueous solutions:

I  3-isopropyl-2,1,3-benzothiadiazinone-(4)-2,2-dioxide, 0.5, 1, 1.5 and 2 kg/ha;
II  3-isopropyl-2,1,3-benzothiadiazinone-(4)-2,2-dioxide, sodium salt, 0.5, 1, 1.5 and 2 kg/ha;
III 5-chloro-4-methyl-2-propionamide thiazole, 0.5, 1, 1.5 and 2 kg/ha;
IV 3-isopropyl-2,1,3-benzothiadiazinone-(4)-2,2-dioxide, dimethylamine salt, 0.5, 1, 1.5 and 2 kg/ha;
V 3-isopropyl-2,1,3-benzothiadiazinone-(4)-2,2-dioxide, diethanolamine salt, 0.5, 1, 1.5 and 2 kg/ha;
I+III, II+III, IV+III and V+III, each at rates of 1.5+0.5, 0.5+1.5 and 1+1 kg/ha.

After 2 to 3 weeks it was ascertained that the compositions had a better herbicidal action than their components, combined with the same crop plant compatibility.

The results are given below:

| Active ingredient kg/ha | I 0.5 | I 0.75 | I 1 | I 1.5 | II 0.5 | II 0.75 | II 1 | II 1.5 | III 0.5 | III 0,75 | III 1 | III 1.5 | IV 0.5 | IV 0.75 | IV 1 | IV 1.5 | V 0.5 | V 0.75 | V 1 | V 1.5 |
|---|---|---|---|---|---|---|---|---|---|---|---|---|---|---|---|---|---|---|---|---|
| Crop plants: | | | | | | | | | | | | | | | | | | | | |
| Triticum aestivum | 0 | 0 | 0 | 0 | 0 | 0 | 0 | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 | 0 | 0 | 0 | 0 | 0 | 0 | 0 |
| Unwanted plants: | | | | | | | | | | | | | | | | | | | | |
| Galium aparine | 30 | 35 | 40 | 60 | 30 | 40 | 45 | 60 | 15 | 18 | 20 | 25 | 28 | 40 | 50 | 60 | 35 | 45 | 60 | 67 |
| Stellaria media | 30 | 40 | 60 | 70 | 20 | 30 | 50 | 70 | 15 | 20 | 25 | 30 | 27 | 35 | 50 | 70 | 24 | 40 | 60 | 80 |
| Alopecurus myosuroides | 2 | 5 | 5 | 10 | 3 | 8 | 12 | 15 | 15 | 17 | 25 | 40 | 5 | 7 | 10 | 16 | 4 | 7 | 12 | 15 |

0 = no damage
100 = complete destruction

| Active ingredient kg/ha | I+III 0.5 1 | I+III 1 0.5 | I+III 0.75 0.75 | II+III 0.5 1 | II+III 1 0.5 | II+III 0.75 0.75 | IV+III 0.5 1 | IV+III 1 0.5 | IV+III 0.75 0.75 | V+III 0.5 1 | V+III 1 0.5 | V+III 0.75 0.75 |
|---|---|---|---|---|---|---|---|---|---|---|---|---|
| Crop plants: | | | | | | | | | | | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Unwanted plants: | | | | | | | | | | | | |
| Galium aparine | 85 | 90 | 90 | 92 | 100 | 95 | 87 | 100 | 95 | 97 | 100 | 100 |
| Stellaria media | 95 | 100 | 100 | 90 | 100 | 90 | 90 | 100 | 97 | 90 | 100 | 100 |
| Alopecurus myosuroides | 70 | 60 | 65 | 70 | 65 | 62 | 76 | 70 | 65 | 72 | 70 | 66 |

0 = no damage
100 = complete destruction

| Active ingredient kg/ha | I 0.5 | I 1 | I 1.5 | I 2 | II 0.5 | II 1 | II 1.5 | II 2 | III 0.5 | III 1 | III 1.5 | III 2 | IV 0.5 | IV 1 | IV 1.5 | IV 2 | V 0.5 | V 1 | V 1.5 | V 2 |
|---|---|---|---|---|---|---|---|---|---|---|---|---|---|---|---|---|---|---|---|---|
| Crop plants | | | | | | | | | | | | | | | | | | | | |
| Triticum aestivum | 0 | 0 | 0 | 0 | 0 | 0 | 0 | 0 | 0 | 0 | 0 | 10 | 0 | 0 | 0 | 0 | 0 | 0 | 0 | 0 |

| Active ingredient kg/ha | I 0.5 | 1 | 1.5 | 2 | II 0.5 | 1 | 1.5 | 2 | III 0.5 | 1 | 1.5 | 2 | IV 0.5 | 1 | 1.5 | 2 | V 0.5 | 1 | 1.5 | 2 |
|---|---|---|---|---|---|---|---|---|---|---|---|---|---|---|---|---|---|---|---|---|
| Hordeum vulgare | 0 | 0 | 0 | 0 | 0 | 0 | 0 | 0 | 0 | 0 | 0 | 10 | 0 | 0 | 0 | 0 | 0 | 0 | 0 | 0 |
| Secale cereale | 0 | 0 | 0 | 0 | 0 | 0 | 0 | 0 | 0 | 0 | 0 | 10 | 0 | 0 | 0 | 0 | 0 | 0 | 0 | 0 |
| Unwanted plants: | | | | | | | | | | | | | | | | | | | | |
| Galium aparine | 30 | 40 | 60 | 75 | 30 | 45 | 60 | 80 | 15 | 20 | 25 | 30 | 28 | 50 | 60 | 75 | 35 | 60 | 67 | 80 |
| Stellaria media | 30 | 60 | 70 | 75 | 20 | 50 | 70 | 80 | 15 | 25 | 30 | 40 | 27 | 50 | 70 | 75 | 24 | 60 | 80 | 90 |
| Alopecurus myosuroides | 2 | 5 | 10 | 20 | 3 | 12 | 15 | 18 | 15 | 25 | 40 | 50 | 5 | 10 | 16 | 24 | 4 | 12 | 15 | 19 |

| Active ingredient kg/ha | I+III 1.5 / 0.5 | 0.5 / 1.5 | 1 / 1 | II+III 1.5 / 0.5 | 0.5 / 1.5 | 1 / 1 | IV+III 1.5 / 0.5 | 0.5 / 1.5 | 1 / 1 | V+III 1.5 / 0.5 | 0.1 / 1.5 | 1 / 1 |
|---|---|---|---|---|---|---|---|---|---|---|---|---|
| Crop plants | | | | | | | | | | | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Unwanted plants: | | | | | | | | | | | | |
| Galium aparine | 100 | 95 | 100 | 100 | 95 | 100 | 100 | 92 | 100 | 100 | 100 | 100 |
| Stellaria media | 100 | 100 | 100 | 100 | 90 | 100 | 100 | 98 | 100 | 100 | 95 | 100 |
| Alopecurus myosuroides | 65 | 84 | 70 | 70 | 83 | 49 | 71 | 84 | 75 | 70 | 85 | 77 |

0 = no damage
100 = complete destruction

I claim:

1. A herbicide composition comprising an inert carrier having dispersed therein a herbicidally effective amount of a mixture of herbicides consisting essentially of
a. a compound of the formula

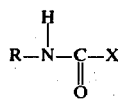

where R denotes lower alkyl of a maximum of 4 carbon atoms, or an alkali metal, alkaline earth metal, ammonium, lower alkyl amine, lower hydroxyalkyl amine or hydrazine salt thereof, and
b. a compound of the formula $$R-N(H)-C(=O)-X$$

where R denotes a 5-chloro-4-methylthiazol-2-yl radical and X denotes lower alkyl in a weight ratio a:b of 3:1 to 1:3.

2. A herbicide composition as claimed in claim 1 wherein said weight ratio is 1:2 and compound (b) is 5-chloro-4-methyl-2-propionamide thiazole.

3. A process for controlling growth of unwanted plants among crop plants which comprises applying to the locus of the plants a herbicidally effective amount of a herbicide composition consisting essentially of a mixture of
a. a compound of the formula

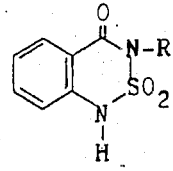

where R denotes lower alkyl of a maximum of 4 carbon atoms, or an alkali metal, alkaline earth metal, ammonium, lower alkyl amine, lower hydroxyalkyl amine or hydrazine salt thereof, and
b. a compound of the formula

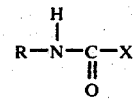

where R denotes a 5-chloro-4-methylthiazol-2-yl radical and X denotes lower alkyl in a weight ratio of a:b of 3:1 to 1:3.

4. A process as claimed in claim 3 wherein said weight ratio is 1:2 and compound (b) is 5-chloro-4-methyl-2-propionamide thiazole.

5. A process as claimed in claim 3 wherein compound a is 3-isopropyl-2,1,3-benzothiadiazinone-(4)-2,2-dioxide.

6. A process as claimed in claim 5 wherein said weight ratio is 1:2 and compound (b) is 5-chloro-4-methyl-2-propionamide thiazole.

7. A herbicide composition as claimed in claim 1 wherein compound a is 3-isopropyl-2,1,3-benzothiadiazinone-(4)-2,2-dioxide.

8. A herbicide composition as claimed in claim 7 wherein said weight ratio is 1:2 and compound (b) is 5-chloro-4-methyl-2-propionamide thiazole.

* * * * *